United States Patent
Jackson et al.

(10) Patent No.: US 11,331,336 B2
(45) Date of Patent: May 17, 2022

(54) PET FOOD COMPOSITIONS

(71) Applicant: HILL'S PET NUTRITION, INC., Topeka, KS (US)

(72) Inventors: Matthew Jackson, Topeka, KS (US); Dennis Jewell, Lawrence, KS (US); Kiran Panickar, Lawrence, KS (US)

(73) Assignee: Hills Pet Nutrition, Inc., Topeka, KS (US)

( * ) Notice: Subject to any disclaimer, the term of this patent is extended or adjusted under 35 U.S.C. 154(b) by 426 days.

(21) Appl. No.: 16/314,556

(22) PCT Filed: Dec. 20, 2018

(86) PCT No.: PCT/US2018/066832
§ 371 (c)(1),
(2) Date: Dec. 31, 2018

(87) PCT Pub. No.: WO2020/131069
PCT Pub. Date: Jun. 25, 2020

(65) Prior Publication Data
US 2021/0220385 A1    Jul. 22, 2021

(51) Int. Cl.

| | |
|---|---|
| *A61K 31/716* | (2006.01) |
| *A23K 20/142* | (2016.01) |
| *A23K 20/163* | (2016.01) |
| *A23K 40/30* | (2016.01) |
| *A23K 50/42* | (2016.01) |
| *A23K 20/105* | (2016.01) |
| *A61P 39/00* | (2006.01) |
| *A61K 9/00* | (2006.01) |
| *A61K 31/19* | (2006.01) |
| *A61K 31/198* | (2006.01) |

(52) U.S. Cl.
CPC .......... *A61K 31/716* (2013.01); *A23K 20/105* (2016.05); *A23K 20/142* (2016.05); *A23K 20/163* (2016.05); *A23K 40/30* (2016.05); *A23K 50/42* (2016.05); *A61K 9/0056* (2013.01); *A61K 31/19* (2013.01); *A61K 31/198* (2013.01); *A61P 39/00* (2018.01)

(58) Field of Classification Search
CPC ...... A23K 20/142; A23K 20/10; A23K 50/42; A23K 40/30; A23K 20/00; A23K 10/00; A23K 20/105; A23K 20/111; A23K 20/163; A61K 31/19; A61K 31/716; A61K 9/0056; A61K 31/198; A61P 39/00
See application file for complete search history.

(56) References Cited

U.S. PATENT DOCUMENTS

| | | |
|---|---|---|
| 5,576,015 A | 11/1996 | Donzis |
| 5,888,514 A | 3/1999 | Weisman |
| 5,968,569 A | 10/1999 | Cavadini et al. |
| 6,214,337 B1 | 4/2001 | Hayen et al. |
| 2003/0077254 A1 | 4/2003 | Ramaekers |
| 2013/0216586 A1 | 8/2013 | LeBrun et al. |
| 2019/0008186 A1 | 1/2019 | Jackson et al. |
| 2019/0014796 A1 | 1/2019 | Jackson et al. |

FOREIGN PATENT DOCUMENTS

| | | | | |
|---|---|---|---|---|
| WO | WO-9004334 A1 * | 5/1990 | ................ | A61P 1/00 |
| WO | 2017/117091 | 7/2017 | | |
| WO | WO 2017/116449 A1 | 7/2017 | | |
| WO | WO-2017117091 A1 * | 7/2017 | ........... | A23K 20/121 |
| WO | 2018/125693 | 7/2018 | | |

OTHER PUBLICATIONS

International Search Report and Written Opinion of the International Searching Authority in International Application No. PCT/US2018/066832, dated Apr. 12, 2019.
Ishida, 2008, "Supplement for pets such as cats and dogs, contains functional raw material, flavor and flavoring agent," JP 2007-306848A and WPI Database AN: 2008-A40512.

* cited by examiner

*Primary Examiner* — Blessing M Fubara

(57) ABSTRACT

Described herein are pet food compositions comprising: a beta glucan; and a pentacyclic triterpene; wherein the weight ratio of the beta glucan to the pentacyclic triterpene, is about 1:1. Methods of making and using these compositions are also described.

15 Claims, 2 Drawing Sheets

PET FOOD COMPOSITIONS

CROSS-REFERENCE TO RELATED APPLICATION

This application is a national stage entry under 35 U.S.C. § 371 of International patent Application No. PCT/US2018/66832, filed Dec. 20, 2018, the contents of which are hereby incorporated herein by reference in their entirety.

BACKGROUND

As reported by the Animal Cancer Foundation, there are approximately sixty-five million dogs and about thirty-two million cats in the United States. Of these, roughly six million new cancer diagnoses are made in dogs and a similar number made in cats each year. Cancer in the companion animal population is a spontaneous disease often similar to cancer seen in humans; some examples include non-Hodgkin's lymphoma, prostate cancer, head and neck carcinoma, mammary carcinoma, melanoma, soft tissue sarcoma and osteosarcoma (see, http://www.acfoundation.org). As such, cancer remains a serious concern for pet owners.

Activation of certain proteins in the immune system serves as an initial checkpoint in the prevention of a tumor formation or spread of cancerous cells. While a sustained pathological increase in pro-inflammatory cytokines and chemokines are detrimental and leads to an inflammatory state, several of these pro-inflammatory proteins also act to reduce the risk of cancer. One such protein that has anti-tumor effects is C-X-C motif chemokine 10 (CXCL10) also known as Interferon gamma-induced protein 10 (IP-10).

CXCL10 is produced by several cells including monocytes and endothelial cells. It plays an important role in various functions including migration and stimulating the adhesion of activated T cells and NK cells both of which are important in antitumor activity. Some evidence suggests that higher levels of CXCL-10 are associated with anti-tumor properties.

Another concern for pet owners is chronic kidney disease. And, while some products of metabolism of bypass dietary components by commensal hindgut microbiome are beneficial (e.g. short chain fatty acids such as butyrate), other postbiotics can have detrimental health effects. In particular, indole-derived and sulfated phenolic postbiotics act as renal toxins and exacerbate chronic renal disease.

Given the prevalence of cancer and chronic renal disease in companion animals, there is a need for maintenance formulations that are capable of reducing the risk of these conditions.

Certain embodiments of the present invention are designed to address these, and other, needs.

BRIEF SUMMARY

Some embodiments of the present invention provide a pet food composition comprising a beta glucan; and a pentacyclic triterpene; wherein the weight ratio of beta glucan to the pentacyclic triterpene is about 1:1. In some embodiments, the pentacyclic triterpene is boswellic acid, or a derivative thereof.

Other embodiments of the present invention provide a composition for reducing postbiotic uremic toxins in a companion animal, comprising: from about 0.1 wt. % to about 0.5 wt. %, of a pentacyclic triterpene; from about 0.1 wt. % to about 0.5 wt. %, of a beta glucan; and a nutritionally complete carrier.

Still further embodiments of the present invention provide methods for: a) reducing postbiotic uremic toxins in a companion animal; b) treating, preventing or ameliorating a symptom of a disease, condition or disorder associated with abnormal levels of C-X-C motif chemokine 10 (CXCL10) in a companion animal; c) treating, preventing or ameliorating a symptom of a disease, condition or disorder associated with elevated levels of postbiotic uremic toxins in a companion animal; and/or d) treating, preventing or ameliorating a symptom associated with chronic kidney disease in a companion animal; comprising: administering any one of the compositions described herein to companion animal in need thereof.

In some embodiments, the present invention provides for the use of any one of the compositions described herein in the manufacture of a pet food composition for: a) reducing postbiotic uremic toxins in a companion animal; b) treating, preventing or ameliorating a symptom of a disease, condition or disorder associated with abnormal levels of C-X-C motif chemokine 10 (CXCL10) in a companion animal; c) treating, preventing or ameliorating a symptom of a disease, condition or disorder associated with elevated levels of postbiotic uremic toxins in a companion animal; and/or d) treating, preventing or ameliorating a symptom associated with chronic kidney disease in a companion animal.

DETAILED DESCRIPTION

Figure 1:
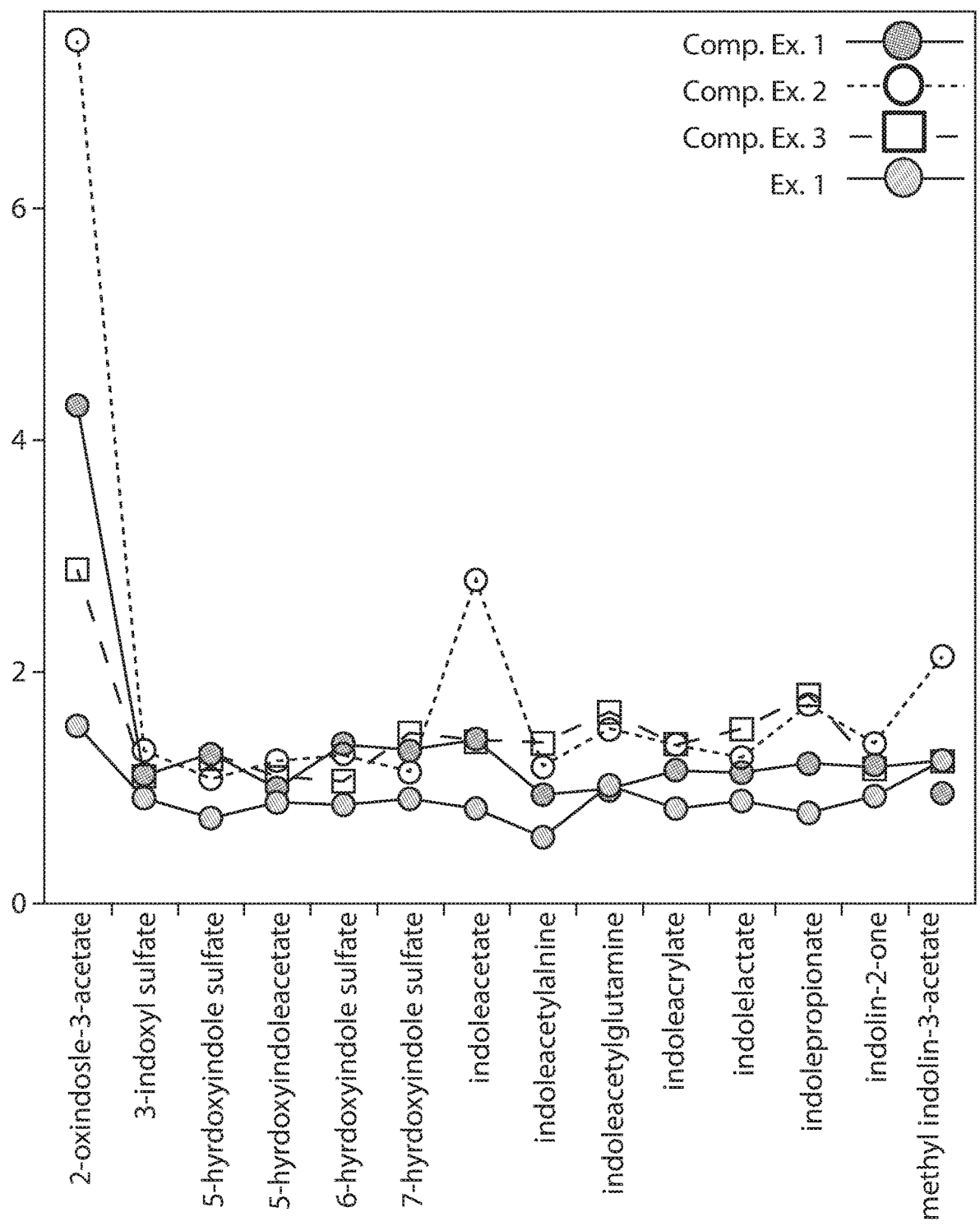
FIG. 1 depicts data demonstrating the unexpected reduction in circulating indole postbiotics provided by an exemplary composition of the present invention.

Some embodiments of the present invention provide a pet food composition comprising a beta glucan; and a pentacyclic triterpene; wherein the weight ratio of beta glucan to the pentacyclic triterpene is about 1:1. In some embodiments, the pentacyclic triterpene is boswellic acid, or a derivative thereof. In other embodiments, the boswellic acid, or derivative thereof, is *Boswellia serrata*.

Other embodiments of the present invention provide a composition for reducing postbiotic uremic toxins in a companion animal, comprising: from about 0.1 wt. % to about 0.5 wt. %, of a pentacyclic triterpene; from about 0.1 wt. % to about 0.5 wt. %, of a beta glucan; and a nutritionally complete carrier. Further embodiments of the present invention provide a composition for reducing postbiotic uremic toxins in a companion animal, comprising: from about 0.1 wt. % to about 0.5 wt. %, of boswellic acid, or a derivative thereof; from about 0.1 wt. % to about 0.5 wt. %, of a beta glucan; and a nutritionally complete carrier.

In some embodiments, the present invention provides a pet food composition comprising: boswellic acid or a derivative thereof. In some embodiments, boswellic acid is selected from alpha, beta, and 11-keto-beta boswellic acids. Derivatives also include the acetyl derivatives.

In some embodiments, the isomers of boswellic acid and its derivatives are preferably naturally occurring, and may be derived from sources known in the art. They may, for example, be synthesized, or obtained from aqueous or ethanolic extracts of an herb of the genus *Boswellia*, preferably from the gum resin of the species *serrata*. See, for example, Sen et al., Carbohydrate Res. 223, 321 (1992) and Ammon et al, Planta Med. 57, 203 (1991).

A suitable source of boswellic acids is an extract of *Boswellia serrata* resin standardized to 60% boswellic acids. Such an extract is available from Ayush Herbs, Inc., Bellevue, Wash. under the name Boswelya Plus.

Some embodiments further comprise a beta glucan. Glucans generally are taken to mean polyglucosans, that is to say mostly naturally occurring unbranched and branched polymers of glucose. These occur in particular in yeasts, cereals (in particular oat and barley cereals), fungi, lichens and algae. Preferably, β-glucans are used inventively, that is to say glucans in which the glucose units are β-(1,3)- and/or β-(1,4)-linked and may have 1,3 and/or 1,6 branches.

If the β-glucans are produced from yeasts, the yeasts preferably used are those of the strains *Candida albicans, Candida cloaceae, Candida tropicalis, Candida utilis, Geotrichum candidum, Hansenula americana, Hansenula anomala, Hansenula wingei, Hansenula arni, Hansenula henricii, Hansenula canadiensis, Hansenula capsulate, Hansenulapolymorpha, Kloeckera brevis, Kloeckera apiculata, Kluyveromyces polysporus, Kluyveromyces bulgaricus, Kluyveromyces fragilis, Pichia fermentans, Pichia kluveri, Pichia pastoris, Pichia polymorpha, Pichia rhodanesis, Pichia ohmeri, Saccharomyces bisporus, Saccharomyces boulardii, Saccharomyces cerevisiae, Saccharomyces capsularis, Saccharomyces delbrueckii, Saccharomyces fermentati, Saccharomyces lugwigii, Saccharomyces microellipsoides, Saccharomyces pastorianus, Saccharomyces rosei, Saccharomyces rouxii, Saccharomyces synnaedendra, Schizosaccharomyces pombe, Torulopsis bovina, Torulopsis glabrata* and in particular wine yeast and baker's yeast.

A number of possibilities exist for producing β-glucans from the yeast cells. In principle, the glucans, in particular β-glucans, are treated with alkaline earth metal hydroxides/alkali metal hydroxides at a low concentration of 0.05-1.0% stepwise or successively also with surfactant-containing (for example lauryl sulfonate-containing) solution at temperatures between 20 and 100° C. For this, numerous protocols are known. After extraction of the cell wall fractions, the residue is gently dried. Yeast cell walls suspended in water or suitably diluted extraction solution, which have a high content of bioavailable β-glucans, can also be produced in this manner. Furthermore, glucans can be produced from yeasts by a combination of mechanical disintegration, purification and freeze-drying and subsequent enzymatic disruption, with subsequent centrifugation.

In the case of a dry product from yeast cell walls, expediently, the dry matter content of the resultant residue should be greater than 90% by weight and the polysaccharide content should be at least 70% by weight (in each case based on the yeast cell wall extract). The bioavailable glucan content in the polysaccharide fraction should expediently be at least 75% by weight. In the case of liquid cell walls or liquid preparations, equivalent contents based on the dry matter are calculated.

Oat extracts or barley extracts in the context of this invention are fractions produced by milling from the cereal species of oaks (genus: *Avena*) or barley (genus: *Hordeum*) which comprise β-glucans typical of these cereal species. Furthermore, these are taken to mean extracts from these cereals which have been produced from these cereals by treatment with suitable solvents and comprise β-glucans. The extracts can be used either in dissolved form or as powder/granules/agglomerates. Various possibilities exist for producing β-glucans from cereals. Some are described in WO 2001/026479, which is expressly incorporated herein by reference. They can be separated into fractions, for example by grinding processes, (for example into the bran fraction, which typically comprises between 7 and 20% by weight of bioavailable β-glucan).

Other isolates containing bioavailable β-glucans from fungi such as linghi (*Ganoderma lucidum*) or shiitake mushroom (*Lentinus edodes*) or *Cortinellus shiitake* or a similar species (described, for example, in "Functional Properties of Edible Mushrooms"; Mattila-P, Suonpää-K, Piironen-V; Nutrition; 16 (7/8) 694-696, 2000) or extracts from lichens (scleroglucan from lichens, *Sclerotium* species, described, for example, in "Isolation and physicochemical characterization of soluble scleroglucan from *Sclerotium rolfsii*"; Siñeriz-F, Molina-OE, Perotti-NI; Carbohydrate Polymers 44 (2001) 41-50), for example the commercial product Polytran® (Pillsburg Co., Delaware 1343, Minneapolis, Minn. 55402; β-1,3-linked D-glucose, to which D-glucose is linked as side chain via β-1,6-bonds) are also a material having bioavailable β-glucans in the context of this invention and can be used as an alternative to abovementioned extracts from yeast cell walls or cereals. This also applies to *laminaria*-containing extracts from brown algae (*laminaria* species) which comprise bioavailable β-(1,3) glucans, occasionally also containing β-(1,6) glycosidic bonds.

In some embodiments, the present invention provides a pet food composition comprising: a beta glucan; and a pentacyclic triterpene. In other embodiments, the pentacyclic triterpene comprises boswellic acid, or a derivative thereof. In further embodiments, the pet food composition comprises: a beta glucan; and boswellic acid, or a derivative thereof; wherein the weight ratio of beta glucan to boswellic acid, or a derivative thereof, is about 1:1. In some embodiments, the boswellic acid, or a derivative thereof, comprises *Boswellia serrata*.

In some embodiments, the beta glucan is produced from a yeast. In other embodiments, the beta glucan comprises beta-1,3-1,6-glucan.

In some embodiments, the boswellic acid, or derivative thereof, is present in an amount of from about 0.1% to about 0.5%, by weight of the composition. In further embodiments, the boswellic acid, or derivative thereof, is present in an amount of about 0.05%, about 0.1%, about 0.15%, about 0.2%, 0.25%, about 0.3%, about 0.35%, about 0.4%, about 0.45%, or about 0.5%, by weight of the composition. Still other embodiments provide pet food compositions wherein the boswellic acid, or derivative thereof, is present in an amount of 0.33%, by weight of the composition.

In some embodiments, the beta glucan is present in an amount of from about 0.1% to about 0.5%, by weight of the composition. In other embodiments, the beta glucan is present in an amount of about 0.05%, about 0.1%, about 0.15%, about 0.2%, 0.25%, about 0.3%, about 0.35%, about 0.4%, about 0.45%, or about 0.5%, by weight of the composition.

In some embodiments, the combined concentration of the beta glucan and boswellic acid, or a derivative thereof, is from about 0.5% to about 1%, by weight of the total composition.

In some embodiments, the pet food composition further comprises an amino acid. In some embodiments, the amino acid is selected from arginine, taurine and glycine. In some embodiments, the amino acid comprises taurine.

In some embodiments, the present invention provides a composition for reducing postbiotic uremic toxins in a companion animal, comprising: from about 0.1 wt. % to about 0.5 wt. %, of boswellic acid, or a derivative thereof; of from about 0.1 wt. % to about 0.5 wt. %, of a beta glucan;

and a nutritionally complete carrier. In further embodiments, the nutritionally complete carrier comprises about 15 wt. % fat, on a dry matter basis of the composition. In some embodiments, the nutritionally complete carrier comprises about 25 wt. % protein, on a dry matter basis of the composition. In other embodiments, the nutritionally complete carrier comprises about 10 wt. % fiber, on a dry matter basis of the composition. In certain embodiments, the nutritionally complete carrier comprises about 8 wt. % moisture.

Other embodiments of the present invention provide methods for: a) reducing postbiotic uremic toxins in a companion animal; b) treating, preventing or ameliorating a symptom of a disease, condition or disorder associated with abnormal levels of C-X-C motif chemokine 10 (CXCL10) in a companion animal; c) treating, preventing or ameliorating a symptom of a disease, condition or disorder associated with elevated levels of postbiotic uremic toxins in a companion animal; and/or d) treating, preventing or ameliorating a symptom associated with chronic kidney disease in a companion animal; comprising: administering any one of the compositions described herein to companion animal in need thereof.

Still further embodiments provide for the use of any one of the compositions described herein in the manufacture of a pet food composition for: a) reducing postbiotic uremic toxins in a companion animal; b) treating, preventing or ameliorating a symptom of a disease, condition or disorder associated with abnormal levels of C-X-C motif chemokine 10 (CXCL10) in a companion animal; c) treating, preventing or ameliorating a symptom of a disease, condition or disorder associated with elevated levels of postbiotic uremic toxins in a companion animal; and/or d) treating, preventing or ameliorating a symptom associated with chronic kidney disease in a companion animal.

In some embodiments, the composition is in the form of a kibble. In further embodiments, the composition is in the form of a multi-layer kibble. Yet other embodiments provide a multi-layer kibble comprising a coating. In some embodiments, the coating comprises a palatant. In some embodiments, the coating further comprises a beta glucan and a boswellic acid, or derivative thereof. In some embodiments, the kibble is formed by extrusion.

In some embodiments, the kibble further comprises a binder. In some embodiments, the binder can comprise any of the following or combinations of the following materials: monosaccharides such as glucose, fructose, mannose, arabinose; di- and trisaccharides such as sucrose, lactose, maltose, trehalose, lactulose; corn and rice syrup solids; dextrins such a corn, wheat, rice and tapioca dextrins; maltodextrins; starches such as rice, wheat, corn, potato, tapioca starches, or these starches modified by chemical modification; alginates, chitosans; gums such as carrageen, and gum arabic; polyols such as glycerol, sorbitol, mannitol, xylitol, erythritol; esters of polyols such as sucrose esters, polyglycol esters, glycerol esters, polyglycerol esters, sorbitan esters; sorbitol; molasses; honey; gelatins; peptides; proteins and modified proteins such as whey liquid, whey powder, whey concentrate, whey isolate, whey protein isolate, high lactose whey by-product, meat broth solids such as chicken broth, chicken broth solids, soy protein, and egg white.

In some embodiments, lipids and lipid derivatives can also be used as binder components. Lipids can be used in combination with water and/or other binder components. Lipids can include plant fats such as soybean oil, corn oil, rapeseed oil, olive oil, safflower oil, palm oil, coconut oil, palm kernel oil, and partially and fully hydrogenated derivatives thereof; animal fats and partially and fully hydrogenated derivatives thereof; and waxes.

In some embodiments, the composition is not prepared by extrusion. In some embodiments, the composition is in a form selected from: a loaf, a stew, a "meat and gravy" form, a gruel, shreds with a moisture content greater than 50%", and a product that could be pushed through a syringe.

As used herein, the term "a companion animal" refers to an animal of any species kept by a caregiver as a pet or any animal of a variety of species that have been widely domesticated as pets, including dogs (*Canis familiaris*) and cats (*Felis domesticus*), whether or not the individual animal is kept solely or partly for companionship. Thus, companion animals include, for example and not limitation, working dogs, farm cats kept for rodent control, pet cats, pet dogs, ferrets, birds, reptiles, rabbits, and fish. In some embodiments, the companion animal is selected from a canine and a feline. In other embodiments, the companion animal is a canine.

As used herein, the term "soluble fiber" means one or more fibers that are readily fermented in the large intestine, e.g., beet pulp, guar gum, chicory root, *Psyllium*, pectin, blueberry, cranberry, squash, apples, oats, beans, citrus, or barley.

In some embodiments, compositions of the present invention may contain an "insoluble fiber" source. In some embodiments, insoluble fiber may be supplied by any of a variety of sources, including cellulose, whole wheat products, wheat oat, corn bran, flax seed, grapes, celery, green beans, cauliflower, potato skins, fruit skins, vegetable skins, peanut hulls, and soy fiber.

In instances when the composition is an animal's food, vitamins and minerals can be included in amounts required to avoid deficiency and maintain health. These amounts are readily available in the art. The Association of American Feed Control Officials (AAFCO) provides recommended amounts of such ingredients for dogs and cats. See Association of American Feed Control Officials. Official Publication, pp. 126-140 (2003). Vitamins useful as food additives include, e.g., vitamin A, vitamin $B_1$, vitamin $B_2$, vitamin $B_6$, vitamin $B_{12}$, vitamin C, vitamin D, vitamin E, vitamin H (biotin), vitamin K, folic acid, inositol, niacin, and pantothenic acid. Minerals and trace elements useful as food additives include calcium, phosphorus, sodium, potassium, magnesium, copper, zinc, choline, and iron salts.

The compositions of the present invention may further contain additives known in the art. Such additives should be present in amounts that do not impair the purpose and effect provided by the invention. Examples of additives include substances with a stabilizing effect, organoleptic substances, processing aids, and substances that provide nutritional benefits.

Stabilizing substances may increase the shelf life of the composition. Suitable examples can include preservatives, antioxidants, synergists and sequestrants, packaging gases, stabilizers, emulsifiers, thickeners, gelling agents, and humectants. Examples of emulsifiers and/or thickening agents include gelatin, cellulose ethers, starch, starch esters, starch ethers, and modified starches.

Additives for coloring, palatability, and nutritional purposes can include colorants, salts (including but not limited to sodium chloride, potassium citrate, potassium chloride, and other edible salts), vitamins, minerals, and flavoring. The amount of such additives in a composition typically is up to about 5% by weight (on a dry matter basis of the composition). Other additives can include antioxidants, omega-3 fatty acids, omega-6 fatty acids, glucosamine, chondroitin sulfate, vegetable extracts, herbal extracts, etc.

The term "palatability", as used herein, encompasses all of the various properties of the food sensed by the animal, such as texture, taste and aroma.

Some embodiments of the present invention comprise a carbohydrate source. The carbohydrate source can comprise cereals, grains, corn, wheat, rice, oats, corn grits, sorghum, grain sorghum/milo, wheat bran, oat bran, amaranth, Durum, and/or semolina.

Some embodiments of the present invention comprise a fat source. The fat source, or fat ingredient, can comprise poultry fat, chicken fat, turkey fat, pork fat, lard, tallow, beef fat, vegetable oils, corn oil, soy oil, cottonseed oil, palm oil, palm kernel oil, linseed oil, canola oil, rapeseed oil, fish oil, menhaden oil, anchovy oil, and/or olestra.

Other embodiments of the present invention comprise additional ingredients. For example, these additional ingredients can include active ingredients, such as sources of fiber, minerals, vitamins, amino acids, carotenoids, antioxidants, fatty acids, glucose mimetics, probiotics, prebiotics, and others.

Sources of fiber can include, for example, fructooligosaccharides (FOS), beet pulp, mannanoligosaccharides (MOS), oat fiber, citrus pulp, carboxymethylcellulose (CMC), guar gum, gum arabic, apple pomace, citrus fiber, fiber extracts, fiber derivatives, dried beet fiber (sugar removed), cellulose, a-cellulose, galactooligosaccharides, xylooligosaccharides, and oligo derivatives from starch, inulin, *Psyllium*, pectins, citrus pectin, guar gum, xanthan gum, alginates, gum arabic, gum talha, beta-glucans, chitins, lignin, celluloses, non-starch polysaccharides, carrageenan, reduced starch, soy oligosaccharides, trehalose, raffinose, stachyose, lactulose, polydextrose, oligodextran, gentiooligosaccharide, pectic oligosaccharide, and/or hemicellulose.

Mineral sources can include, for example, sodium selenite, monosodium phosphate, calcium carbonate, potassium chloride, ferrous sulfate, zinc oxide, manganese sulfate, copper sulfate, manganous oxide, potassium iodide, and/or cobalt carbonate. In some embodiments, pecan shells may also be a source of lignin-based fiber.

Suitable vitamins may include choline chloride, vitamin E, ascorbic acid, vitamin A acetate, calcium pantothenate, pantothenic acid, biotin, thiamine mononitrate (source of vitamin B1), vitamin B12 supplement, niacin, riboflavin supplement (source of vitamin B2), inositol, pyridoxine hydrochloride (source of vitamin B6), vitamin D3 supplement, folic acid, vitamin C, and/or ascorbic acid.

Sources of polyphenols ingredients can include tea extract, rosemary extract, rosemarinic acid, coffee extract, pecan shells, caffeic acid, turmeric extract, blueberry extract, grape extract, grapeseed extract, and/or soy extract.

Sources of amino acids can include 1-Tryptophan, Taurine, Histidine, Carnosine, Alanine, Cysteine, Arginine, Methionine, Tryptophan, Lysine, Asparagine, Aspartic acid, Phenylalanine, Valine, Threonine, Isoleucine, Histidine, Leucine, Glycine, Glutamine, Taurine, Tyrosine, Homocysteine, Ornithine, Citruline, Glutamic acid, Proline, and/or Serine.

Sources of carotenoids may include lutein, astaxanthin, zeaxanthin, bixin, lycopene, and/or beta-carotene. Sources of antioxidant ingredients can include tocopherols (vitamin E), vitamin C, vitamin A, plant-derived materials, carotenoids (described above), selenium, and/or CoQ10 (Coenzyme Q10). Sources of fatty acid ingredients can include arachidonic acid, alpha-linoleic acid, gamma linolenic acid, linoleic acid, eicosapentanoic acid (EPA), docosahexanoic acid (DHA), and/or fish oils as a source of EPA and/or DHA.

Sources of glucose mimetics can include glucose anti-metabolites including 2-deoxy-D-glucose, 5-thio-D-glucose, 3-O-methylglucose, anhydrosugars including 1,5-anhydro-D-glucitol, 2,5-anhydro-D-glucitol, and 2,5-anhydro-D-mannitol, mannoheptulose, and/or avocado extract comprising mannoheptulose.

Still other ingredients may include beef broth, brewers dried yeast, egg, egg product, flax meal, DL methionine, amino acids, leucine, lysine, arginine, cysteine, cystine, aspartic acid, polyphosphates, sodium pyrophosphate, sodium tripolyphosphate; zinc chloride, copper gluconate, stannous chloride, stannous fluoride, sodium fluoride, triclosan, glucosamine hydrochloride, chondroitin sulfate, green lipped mussel, blue lipped mussel, methyl sulfonyl methane (MSM), boron, boric acid, phytoestrogens, phytoandrogens, genistein, diadzein, L-carnitine, chromium picolinate, chromium tripicolinate, chromium nicotinate, acid/base modifiers, potassium citrate, potassium chloride, calcium carbonate, calcium chloride, sodium bisulfate; *Eucalyptus*, lavender, peppermint, plasticizers, colorants, flavorants, sweeteners, buffering agents, slip aids, carriers, pH adjusting agents, natural ingredients, stabilizers, biological additives such as enzymes (including proteases and lipases), chemical additives, coolants, chelants, denaturants, drug astringents, emulsifiers, external analgesics, fragrance compounds, humectants, opacifying agents (such as zinc oxide and titanium dioxide), anti-foaming agents (such as silicone), preservatives (such as butylated hydroxytoluene (BHT) and butylated hydroxyanisole (BHA), propyl gallate, benzalkonium chloride, EDTA, benzyl alcohol, potassium sorbate, parabens and mixtures thereof), reducing agents, solvents, hydrotropes, solubilizing agents, suspending agents (non-surfactant), solvents, viscosity increasing agents (aqueous and non-aqueous), sequestrants, and/or keratolytics.

Suitable probiotics may include one or more bacterial probiotic microorganisms suitable for pet consumption and effective for improving the microbial balance in the pet gastrointestinal tract or for other benefits, such as disease or condition relief or prophylaxis, to the pet. Various probiotic microorganisms known in the art. In some embodiments, the probiotic component may be selected from bacteria, yeast or microorganism of the genera *Bacillus, Bacteroides, Bifidobacterium, Enterococcus* (e.g., *Enterococcus faecium* DSM 10663 and *Enterococcus faecium* SF68), *Lactobacillus, Leuconostroc, Saccharomyces, Candida, Streptococcus*, and mixtures of any thereof. In other embodiments, the probiotic may be selected from the genera *Bifidobacterium, Lactobacillus*, and combinations thereof. Those of the genera *Bacillus* may form spores. In further embodiments, the probiotic does not form a spore. Non-limiting examples of lactic acid bacteria suitable for use herein include strains of *Streptococcus lactis, Streptococcus cremoris, Streptococcus diacetylactis, Streptococcus thermophilus, Lactobacillus bulgaricus, Lactobacillus acidophilus* (e.g., *Lactobacillus acidophilus* strain DSM 13241), *Lactobacillus helveticus, Lactobacillus bifidus, Lactobacillus casei, Lactobacillus lactis, Lactobacillus plantarum, Lactobacillus rhamnosus, Lactobacillus delbrukii, Lactobacillus thermophilus, Lactobacillus fermentii, Lactobacillus salvarius, Lactobacillus reuteri, Bifidobacterium longum, Bifidobacterium infantis, Bifidobacterium bifidum, Bifidobacterium animalis, Bifidobacterium pseudolongum*, and *Pediococcus cerevisiae*, or mixtures of any thereof. In specific embodiments, the probiotic-enriched coating may comprise the bacterial strain *Bifidobacterium animalis* AHC7 NCIMB 41199.

As used herein, the term "kibble" includes a particulate pellet like component of animal feeds, such as dog and cat feeds, typically having a moisture, or water, content of less than 12% by weight. Kibbles may range in texture from hard to soft. Kibbles may range in internal structure from expanded to dense. Kibbles may be formed by an extrusion process. In non-limiting examples, a kibble can be formed from a core and a coating to form a kibble that is coated, also called a coated kibble. It should be understood that when the term "kibble" is used, it can refer to an uncoated kibble or a coated kibble.

Some embodiments of the present invention comprise a protein source. The protein source, or protein ingredient, can comprise chicken meals, chicken, chicken by-product meals, lamb, lamb meals, turkey, turkey meals, beef, beef by-products, viscera, fish meal, enterals, kangaroo, white fish, venison, soybean meal, soy protein isolate, soy protein concentrate, corn gluten meal, corn protein concentrate, distillers dried grains, and/or distillers dried grains solubles and single-cell proteins, for example yeast, algae, and/or bacteria cultures.

Embodiments of the present invention will now be further described by way of the following, non-limiting, examples.

EXAMPLES

Example 1

Diets were formulated according to AAFCO (American Association of Feed Control Officials) and NRC (National Research Council) nutrition recommendation. The finished kibble was produced by extrusion, dried and coated with palatants. In diets containing the *Boswellia* and/or beta glucan, the ingredients were coated onto the exterior of dried kibble along with palatants. All diets were canine maintenance formulations. A first comparative formula (Comp. Ex. 1) contained only the nutritional components of the formulation without the experimental ingredients (i.e., no *Boswellia* or beta glucan). Two additional comparative formulas were also prepared and evaluated; these contained either *Boswellia* or beta glucan; and are identified as Comp. Ex. 2 and Comp. Ex. 3 herein. In contrast, the exemplary composition of the present invention contained both *Boswellia* and beta glucan at the same levels found individually in Comp. Ex. 2 and Comp. Ex. 3. All four compositions are described below in Table 1.

TABLE 1

| Ingredients | Comp. Ex. 1 | Comp. Ex. 2 | Comp. Ex. 3 | Ex. 1 |
|---|---|---|---|---|
| | Wt. % | | | |
| Chicken, ground, fresh | 14 | 14 | 14 | 14 |
| Barley, pearled, cracked | 13.7521 | 13.7521 | 13.7521 | 13.7521 |
| Sorghum, whole | 12.6 | 12.6 | 12.6 | 12.6 |
| Wheat, red, whole | 13.99 | 13.66 | 13.69 | 13.36 |
| Corn, yellow, whole | 11.99 | 11.99 | 11.99 | 11.99 |
| Corn, gluten, meal | 9.63 | 9.63 | 9.63 | 9.63 |
| Chicken Meal | 8.985 | 8.985 | 8.985 | 8.985 |
| Boswellic Acids | — | 0.33 | — | 0.33 |
| Pork Fat | 2.7303 | 2.7303 | 2.7303 | 2.7303 |
| Beet pulp | 2.5 | 2.5 | 2.5 | 2.5 |
| Chicken liver digest | 2.5 | 2.5 | 2.5 | 2.5 |
| Flavor | 1.3 | 1.3 | 1.3 | 1.3 |
| Lactic acid | 1.2 | 1.2 | 1.2 | 1.2 |
| Flax seed | 0.95 | 0.95 | 0.95 | 0.95 |
| Salt(s) | 0.3911 | 0.3911 | 0.3911 | 0.3911 |

TABLE 1-continued

| Ingredients | Comp. Ex. 1 | Comp. Ex. 2 | Comp. Ex. 3 | Ex. 1 |
|---|---|---|---|---|
| | Wt. % | | | |
| Calcium carbonate | 0.301 | 0.301 | 0.301 | 0.301 |
| Choline chloride | 0.2446 | 0.2446 | 0.2446 | 0.2446 |
| Beta-Glucan | — | — | 0.3 | 0.3 |
| Vitamins and Minerals | 0.2201 | 0.2201 | 0.2201 | 0.2201 |
| Vitamin Premix | 0.0937 | 0.0937 | 0.0937 | 0.0937 |
| Mineral Premix | 0.0578 | 0.0578 | 0.0578 | 0.0578 |
| Oat Fiber, Fruit, Vegetable blend | 0.04 | 0.04 | 0.04 | 0.04 |
| Taurine | 0.033 | 0.033 | 0.033 | 0.033 |
| Total | 100 | 100 | 100 | 100 |

The exemplary composition of the present invention described in Table 1 (above) is not prepared by extrusion, while the comparative examples may be prepared by extrusion.

Example 2

An IACUC approved clinical dietary intervention protocol was implemented which enrolled healthy canine subjects randomized to four groups based on age, weight and sex. Dogs were assessed as healthy by markers of biochemical and clinical health. The study was a caretaker-blinded, longitudinal design in a 2×2 format (+/−*Boswellia*, +/−beta glucan).

Circulating cytokines were assessed by enzyme linked immunosorbent assay (ELISA) in multi-plex format and expressed in pictograms per milliliter (pg/ml). Whole blood ex vivo culture was performed on blood drawn from fasted dogs. Two blood culture tubes were drawn from each dog that had been fed one of the four experimental diets for 28 days. One tube contained blood culture media to sustain blood cell activity (Control Tube). A second tube contained the same media, but also included a proinflammatory compound (lipopolysaccharide, LPS) in order to assess the capacity of the compositions to enhance canonical immune activation (LPS Tube). In the Control Tube, whole blood was left unperturbed to continue immune processes set in place by the state of the dog's nutrition prior to the blood draw. Although an overtly clinically healthy population, dogs had measurable levels of the anti-tumorigenic cytokine IP-10. Increased levels of cytokine IP-10 in the Control Tube indicates an increased anti-tumorigenic state in dogs. Increased levels of cytokine IP-10 in the LPS Tube indicates a capacity to enhance an immunologically induced anti-tumorigenic state in dogs.

Surprisingly, the exemplary composition of the present invention increased IP-10 in both the Control and LPS Tubes, indicating that compositions of the present invention have inherent IP-10 inducing effect, but also enhances canonical endogenous activation pathways. These results are described below in Table 2 (Control Tube) and Table 3 (LPS Tube).

TABLE 2

Control Tube

| Composition | IP-10 Level* LN (pg/ml) |
|---|---|
| Ex. 1 | 0.99 |
| Comp. Ex. 2 | 0.16 |
| Comp. Ex. 3 | 0.01 |

*IP-10 Levels reported as the difference from Comp. Ex. 1, which is a negative control that does not include a source of either Boswellia or beta glucan.

TABLE 3

LPS Tube

| Composition | IP-10 Level* LN (pg/ml) |
|---|---|
| Ex. 1 | 0.83 |
| Comp. Ex. 2 | 0.24 |
| Comp. Ex. 3 | (−) 0.02 |

*IP-10 Levels reported as the difference from Comp. Ex. 1, which is a negative control that does not include a source of either Boswellia or beta glucan.

As the data described above in Tables 2 and 3 demonstrates, compositions of the present invention, comprising *Boswellia* and beta glucan, provide a synergistic increase in cytokine interferon gamma-induced protein 10 (IP-10) levels.

A comparison of the comparative formulas and the exemplary composition of the present invention shows that the diets contained the same overt nutritional qualities while varying in their inclusion of the experimental ingredients—*Boswellia* (boswellic acids) and beta glucan (beta-1,3-1,6-glucans). All diets were formulated to the same following predicted values (dry matter basis except moisture): Fat (14.6 g/100 g), Protein (24.8 g/100 g), Nitrogen Free Extract (52.8 g/100 g), Fiber (10 g/100 g), Ash (5.8 g/100 g), Moisture (8 g/100 g), Atwater Energy (3954 kcal/kg). Since there were no foreseeable differences in macronutrient makeup, nor were there qualitative differences in ingredients other than the experimental ingredients, it follows that the results observed by the present inventors are driven by the unique and inventive combination of *Boswellia* and beta glucan.

Example 3

An IACUC approved clinical dietary intervention protocol was implemented which enrolled healthy canine subjects randomized to four groups based on age, weight and sex. Dogs were assessed as healthy by markers of biochemical and clinical health. The study was a caretaker-blinded, longitudinal design in a 2×2 format.

A global metabolomics screen was performed on serum samples drawn from each dog that had been fed one of the four experimental diets for 28 days. In brief, serum was lyophilized and extracted with methanol:water to liberate metabolites from serum matrix. Metabolomics was performed by LC-MS with relative fold quantitation.

Postbiotic indole levels in blood serum drawn from dogs fed an exemplary composition of the present invention (Ex. 1) and three comparative compositions (Comp. Ex. 1-Comp. Ex. 3) are compared. As shown in FIG. 1, an exemplary composition of the present invention comprising the combination of *Boswellia* and beta glucan reduces levels of indole-based postbiotic uremic toxins more consistently, and to a greater extent, than comparative compositions which contain either *Boswellia* or beta glucan alone. There was a statistically significant effect of treatment as indicated by multivariate ANOVA (MANOVA; $p<0.05$).

Example 4

An assessment of was done on the magnitude of the effect of an exemplary composition of the present invention (Ex. 1) relative to the individual effects of the comparative compositions (Comp. Ex. 2 and Comp. Ex. 3) added together, to evaluate the degree to which the co-feeding of *Boswellia* and beta glucan concurrently can produce an effect greater than the individual but added effects of those diets consumed separately. The results are described below in Table 4.

TABLE 4

| Indole Postbiotic | Comp. Ex. 2 | Comp. Ex. 3 | Comp. Ex. 2 + Comp. Ex. 3 | Ex. 1 |
|---|---|---|---|---|
| | Least-squared Group Means (Relative Fold Levels) | | | |
| 2-oxindole-3-acetate | 3.15 | (−) 1.40 | 1.75 | (−) 2.77 |
| 3-indoxyl sulfate | 0.21 | (−) 0.01 | 0.20 | (−) 0.20 |
| 5-hydroxyindole sulfate | (−) 0.21 | (−) 0.08 | (−) 0.29 | (−) 0.55 |
| 5-hydroxyindole acetate | 0.24 | 0.12 | 0.36 | (−) 0.11 |
| 6-hydroxyindole acetate | (−) 0.08 | (−) 0.32 | (−) 0.41 | (−) 0.52 |
| 7-hydroxyindole acetate | (−) 0.18 | 0.15 | (−) 0.03 | (−) 0.42 |
| Indoleacetate | 1.37 | (−) 0.02 | 1.35 | (−) 0.60 |
| Indoleacetylalanine | 0.24 | 0.46 | 0.70 | (−) 0.36 |
| Indoleacetylglutamine | 0.51 | 0.66 | 1.18 | 0.03 |
| Indoleacrylate | 0.21 | 0.23 | 0.44 | (−) 0.32 |
| Indolelactate | 0.13 | 0.37 | 0.51 | (−) 0.24 |
| Indolepropionate | 0.50 | 0.60 | 1.10 | (−) 0.43 |
| Indolin-2-one | 0.21 | (−) 0.01 | 0.20 | (−) 0.25 |
| Methyl indole-3-acetate | 1.18 | 0.29 | 1.47 | 0.28 |

The data described in Table 4 (above) demonstrates that compositions of the present invention comprising a combination of *Boswellia* and beta glucan provide a synergistic reduction in indole postbiotic uremic toxins. These results were surprising in light of the results obtained from the comparative formulas which contained either *Boswellia* or beta glucan alone.

Example 5

Figure 2:
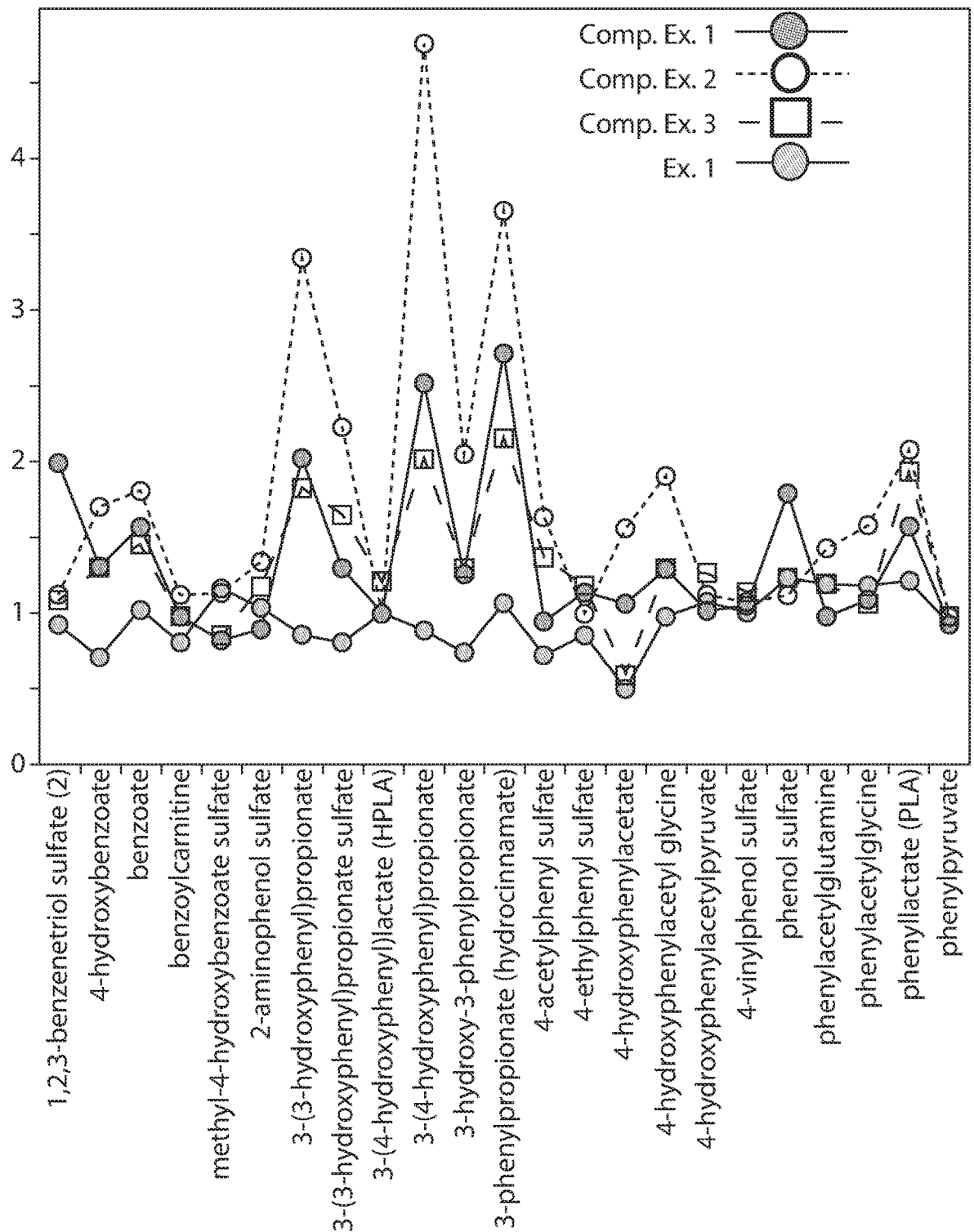
FIG. 2 depicts data demonstrating the unexpected reduction in circulating phenol postbiotics provided by an exemplary composition of the present invention.

Postbiotic phenol levels in blood serum drawn from dogs fed an exemplary composition of the present invention (Ex. 1) and three comparative compositions (Comp. Ex. 1-Comp. Ex. 3) are compared. As shown in FIG. 2, an exemplary composition of the present invention comprising the combination of *Boswellia* and beta glucan reduces levels of phenol-based postbiotic uremic toxins more consistently, and to a greater extent, than comparative compositions which contain either *Boswellia* or beta glucan alone. There was a statistically significant effect of treatment as indicated by multivariate ANOVA (MANOVA; $p<0.05$).

Example 6

An assessment of was done on the magnitude of the effect of an exemplary composition of the present invention (Ex. 1) relative to the individual effects of the comparative compositions (Comp. Ex. 2 and Comp. Ex. 3) added together, to evaluate the degree to which the co-feeding of *Boswellia* and beta glucan concurrently can produce an effect greater than the individual but added effects of those diets consumed separately. The results are described below in Table 5.

TABLE 5

| Phenol Postbiotic | Comp. Ex. 2 | Comp. Ex. 3 | Comp. Ex. 2 + Comp. Ex. 3 | Ex. 1 |
|---|---|---|---|---|
| | Least-squared Group Means (Relative Fold Levels) | | | |
| 1,2,3-benezenetriol sulfate | (−) 0.87 | (−) 0.90 | (−) 1.77 | (−) 1-07 |
| 4-hydroxybenzoate | 0.40 | 0.00 | 0.40 | (−) 0.59 |
| Benzoate | 0.23 | (−) 0.11 | 0.12 | (−) 0.55 |
| Benzoyl carnitine | (−) 0.13 | (−) 0.01 | 0.12 | (−) 0.18 |
| Methyl-4-hydroxybenzoate sulfate | 0.32 | 0.06 | 0.38 | 0.35 |
| 2-aminophenol sulfate | 0.45 | 0.29 | 0.73 | 0.15 |
| 3-(3-hydroxyphenol)-propionate | 1.32 | (−) 0.19 | 1.12 | (−) 1.17 |
| 3-(3-hydroxyphenol)-propionate sulfate | 0.93 | 0.35 | 1.29 | (−) 0.49 |
| 3-(4-hydroxyphenyl)-lactate | 0.00 | 0.23 | 0.23 | 0.01 |
| 3-(4-hydroxyphenyl)-propionate | 2.24 | (−) 0.50 | 1.74 | (−) 1.63 |
| 3-hydroxy-3-phenyl propionate | 0.79 | 0.04 | 0.83 | (−) 0.52 |
| 3-phenyl propionate | 0.94 | (−) 0.56 | 0.38 | (−) 1.65 |
| 4-acetylphenyl sulfate | 0.68 | 0.42 | 1.10 | (−) 0.23 |
| 4-ethylphenyl sulfate | 0.13 | 0.06 | (−) 0.08 | (−) 0.28 |
| 4-hydroxyphenyl acetate | 0.50 | (−) 0.46 | 0.03 | (−) 0.56 |
| 4-hydroxyphenylacetatoyl carnitine | 1.34 | 0.19 | 1.53 | (−) 0.22 |
| 4-hydroxyphenylacetyl glycine | 0.61 | 0.02 | 0.62 | (−) 0.31 |
| 4-hydroxyphenyl pyruvate | 0.11 | 0.25 | 0.36 | 0.06 |
| 4-vinylphenol sulfate | 0.02 | 0.11 | 0.13 | (−) 0.04 |
| Phenol sulfate | (−) 0.67 | (−) 0.55 | (−) 1.21 | (−) 0.56 |
| Phenylacetyl glutamine | 0.45 | 0.22 | 0.67 | 0.21 |
| Phenylacetyl glycine | 0.49 | (−) 0.03 | 0.46 | 0.09 |
| Phenyl lactate | 0.50 | 0.37 | 0.87 | (−) 0.36 |
| Phenyl pyruvate | 0.07 | 0.06 | 0.12 | 0.00 |

The data described in Table 5 (above) demonstrates that compositions of the present invention comprising a combination of *Boswellia* and beta glucan provide a synergistic reduction in certain phenol postbiotic uremic toxins. These results were surprising in light of the results obtained from the comparative formulas which contained either *Boswellia* or beta glucan alone.

In summary, as illustrated by the results described in the Examples, namely FIGS. 1 and 2; and Tables 2-5, compositions of the present invention comprising—in relevant part—a combination of *Boswellia* and beta glucan, decrease circulating uremic toxins in a manner greater than could have been expected by either experimental ingredient alone.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A pet food composition comprising:
   a beta glucan, wherein the beta glucan is present in an amount of from about 0.1 wt % to about 0.5 wt %, based on the total weight of the pet food composition; and
   a pentacyclic triterpene, wherein the pentacyclic triterpene comprises boswellic acids, wherein the boswellic acids are present in an amount of from about 0.1 wt % to about 0.5 wt %, based on the total weight of the pet food composition;
   wherein the weight ratio of the beta glucan to the boswellic acids, is about 1:1, and
   wherein the beta glucan and the pentacyclic triterpene are present in amounts effective to synergistically increase cytokine interferon gamma-induced protein (IP-10) levels in a canine, synergistically reduce levels of indole-based postbiotic uremic toxins in a canine, and/or synergistically reduce phenol-based postbiotic uremic toxins in a canine.

2. The pet food composition according to claim 1, wherein the beta glucan is produced from a yeast.

3. The pet food composition according to claim 1, wherein the beta glucan comprises beta-1,3-1,6-glucan.

4. The pet food composition according to claim 1, wherein the pentacyclic triterpene is present in an amount of about 0.3%, by weight of the composition.

5. The pet food composition according to claim 1, wherein the beta glucan is present in an amount of about 0.3%, by weight of the composition.

6. The pet food composition according to claim 1, further comprising an amino acid.

7. The pet food composition according to claim 6, wherein the amino acid comprises arginine, taurine, glycine, or combinations thereof.

8. The pet food composition according to claim 1, wherein the combined concentration of the beta glucan and pentacyclic triterpene is from about 0.5% to about 1%, by weight of the total composition.

9. The pet food composition of claim 1, wherein the boswellic acids are present in an amount of about 0.3 wt %, based on the total weight of the pet food composition, and wherein the beta glucan is present in an amount of about 0.3 wt %, based on the total weight of the pet food composition.

10. The pet food composition according to claim 1, wherein the composition is in the form of a multi-layer kibble.

11. The pet food composition according to claim 10, wherein the multi-layer kibble comprises a coating.

12. The pet food composition according to claim 11, wherein the coating comprises a palatant.

13. The pet food composition according to claim 11, wherein the coating further comprises the beta glucan and the boswellic acid, or derivative thereof.

14. The pet food composition according to claim 1, wherein the composition is not prepared by extrusion.

15. A method for:
   a) reducing postbiotic uremic toxins in a canine;
   b) treating, preventing or ameliorating a symptom of a disease, condition or disorder associated with abnormal levels of C-X-C motif chemokine 10 (CXCL10) in a canine;
   c) treating, preventing or ameliorating a symptom of a disease, condition or disorder associated with elevated levels of postbiotic uremic toxins in a canine; and/or
   d) treating, preventing or ameliorating a symptom associated with chronic kidney disease in a canine;
   comprising:
   administering the pet food composition of claim 1 to the canine in need thereof.

* * * * *